United States Patent [19]

Kamei et al.

[11] Patent Number: 4,855,133
[45] Date of Patent: Aug. 8, 1989

[54] COMPOSITION FOR ATTRACTING FLIES

[75] Inventors: Masaharu Kamei, Naka; Tsutomu Negishi, Tokushima; Masaru Nishikawa, Itano; Kimishiro Kishino, Tokushima, all of Japan

[73] Assignee: Earth Chemical Company, Limited, Ako, Japan

[21] Appl. No.: 31,068

[22] PCT Filed: Jul. 18, 1986

[86] PCT No.: PCT/JP86/00373

§ 371 Date: Jul. 16, 1987

§ 102(e) Date: Jul. 16, 1987

[87] PCT Pub. No.: WO87/00401

PCT Pub. Date: Jan. 29, 1987

[30] Foreign Application Priority Data

Jul. 18, 1985 [JP] Japan .................................. 60-158835
Jul. 26, 1985 [JP] Japan .................................. 60-166358
Jul. 26, 1985 [JP] Japan .................................. 60-166359
Aug. 16, 1985 [JP] Japan .................................. 60-180749

[51] Int. Cl.$^4$ ..................... A01N 25/00; A01N 43/08; A01N 53/00
[52] U.S. Cl. ..................................... 424/84; 514/461; 514/531
[58] Field of Search ................... 424/84; 514/461, 531

[56] References Cited

U.S. PATENT DOCUMENTS 4,205,066 5/1980 Hennart et al. ..................... 424/84
4,564,631 1/1986 Elbert et al. ....................... 424/84

FOREIGN PATENT DOCUMENTS 2928204 1/1980 Fed. Rep. of Germany ........ 424/84
56-115706 11/1981 Japan .................................. 424/84
901693 7/1962 United Kingdom ................ 424/84

OTHER PUBLICATIONS

The Merck Index, 10th Ed., (1983), #7041 and #1228.

Primary Examiner—Allen J. Robinson
Attorney, Agent, or Firm—Armstrong, Nikaido, Marmelstein, Kubovcik & Murray

[57] ABSTRACT

The invention provides a fly attracting composition characterized by:
  (a) containing a fly attracting compound at least one sex pheromone selected from the group consisting of 9-tricosene, cis-9-tricosene, 10-methyl-9-tricosene, cis-2-methyl-8-docosene, cis-9-docosene, cis-8-docosene and cis-10-tricosene,
  (b) having a yellowish red color in the range of 2.5R to 2.5YR in hue, and
  (c) being in the form of a granular preparation about 0.5 to about 5 mm in mean grain size.

9 Claims, No Drawings

COMPOSITION FOR ATTRACTING FLIES

The present invention relates to compositions for attracting flies to capture and kill them. The invention also relates to attracting-insecticidal compositions for attracting and killing flies and to attractant-bait compositions for poisoning flies by attracting the flies and inducing them to ingest the composition.

Unexamined Japanese Patent Publication SHO No. 56-115706 discloses that flies are attracted to yellow-colored substances having a hue of 5YR to 7.5GY according to the standard prescribed in JIS Z 8721. However, the attracting effect of the yellow-colored substances of this hue on flies is insufficient and in no way satisfactory.

On the other hand, it is also known that 9-tricosene, cis-9-tricosene, etc. have a fly attracting effect as sex pheromones of flies. Nevertheless, the attracting effect of these sex pheromones is also insufficient, so that the fly controlling agents incorporating these pheromones as attractants are still low in controlling efficiency.

The present invention provides a fly attracting composition having an exceedingly higher attracting effect on flies than is achievable by the prior art mentioned.

The invention further provides an attracting-insecticidal composition for attracting flies very effectively and controlling them.

The invention further provides an attractant-bait composition for attracting flies very effectively and causing them to be attracted to the bait with enhanced tenacity so that the insecticidal component thereof can be taken into the body in an increased amount to completely control the flies.

These and other objects of the present invention will become apparent from the following description.

The fly attracting composition of the present invention is characterized by:

(a) containing as a fly attracting compound at least one sex pheromone selected from the group consisting of 9-tricosene, cis-9-tricosene, 10-methyl-9-tricosene, cis-2-methyl-8-docosene, cis-9-docosene, cis-8-docosene and cis-10-tricosene, (b) having a yellowish red color in the range of 2.5R to 2.5YR in hue, and (c) being in the form of a granular preparation about 0.5 to about 5 mm in mean grain size.

The fly attracting compound to be used in the present invention is known as a sex pheromone of flies having a fly attracting effect, but the effect is low, whereas our research has revealed that when the preparation containing the compound has a yellowish red color in the range of 2.5R to 2.5YR in hue and is in the form of grains having a mean size in the specific range of about 0.5 to about 5 mm, the preparation unexpectedly exhibits a surprisingly high attracting effect on flies. The high fly attracting effect is available only when the attracting compound, hue and form of the preparation are as specified above in combination. Such a remarkable attracting effect can not be obtained if other attracting compounds are used, or if the hue of the preparation is outside the specified range of 2.5R to 2.5YR, or if the preparation is not granular or is outside the above range in grain size even when granular.

The attracting compound to be used for the present invention is a sex pheromone selected from among 9-tricosene, cis-9-tricosene, 10-methyl-9-tricosene, cis-2-methyl-8-docosene, cis-9-docosene, cis-8-docosene and cis-10-tricosene. Among these, cis-9-tricosene is especially preferable. According to the present invention at least one of these compounds is used. The concentration of the attracting compound in the preparation is usually about 0.01 to about 15 wt. %, preferably about 0.02 to 4 wt. %, although widely variable.

It is essential that the fly attracting composition of the present invention exhibit a yellowish red color in the range of 2.5R to 2.5YR in hue according to the standard prescribed in JIS Z 8721. If the hue has a closer resemblance to red off 2.5R or to yellow off 2.5YR, the contemplated high fly attracting effect is not available. More preferably, the hue is in the range of 7.5R to 2.5YR. It is also desirable that the present preparation having the above-specified hue be at least 4, more preferably at least 5, in lightness and at least 6, more preferably at least 7, in saturation according to JIS Z 8721.

The pigments useful for imparting such a color to the composition of the present invention include not only usual pigments (coloring substances) but also fluorescent or luminescent substances. Examples of suitable pigments are as follows.

* Red No. 2 (Amaranth, Acid Red 27, sodium 1-(4-sulfo-1-naphthylazo)-2-naphthol-3,6-disulfonate)
* Red No. 3 (Erythrosine, Acid Red 51, 9-o-carboxyphenyl-6-hydroxy-2,4,5,7-tetraiodo-3-isoxanthonedisodium)
* Red No. 102 (New Coccine, Acid Red 18, trisodium 1-(4-sulfone-1-naphthylazo)-2-naphthol-6,8-disulfonate)
* Red No. 104-(1) (Phloxine B, Acid Red 92, 9-(3,4,5,6-tetrachloro-o-carboxyphenyl)-6-hydroxy-2,4,5,7-tetrabromo-3-isoxanthonedisodium)
* Red No. 105-(1) (Rose Bengale, Acid Red 94, 9-(3,4,5,6-tetrachloro-o-carboxyphenyl)-6-hydroxy-2,4,5,7-tetraiodo-3-isoxanthonedisodium)
* Red No. 106 (Acid Red, Acid Red 52, 9-(4'-sulfo-2'-sulfoniumphenyl)-6-diethylamino-3-(N,N-diethylimino)-3-isoxanthenemonosodium)
* Yellow No. 4 (Tartrazine, Acid Yellow 23, 3-carboxy-5-hydroxy-1-p-sulfophenyl-4-p-sulfophenylazopyrazoletrisodium)
* Yellow No. 5 (Sunset Yellow FCF, Acid Yellow 3, disodium 1-p-sulfophenylazo-2-naphthol-6-sulfonate)
* Red No. 201 (Lithol Rubine B, Pigment Red 57-1, monosodium 4-(o-sulfo-p-tolylazo)-3-hydroxy-2-naphthoate)
* Red No. 202 (Lithol Rubine BCA, Pigment Red 57-1, calcium 4-(o-sulfo-p-tolylazo)-3-hydroxy-2-naphthoate)
* Red No. 203 (Lake Red C, Pigment Red 533(Na), 1-(4-chloro-o-sulfo-5-tolylazo)-2-naphthol-monosodium)
* Red No. 204 (Lake Red CBA, Pigment Red 53(Ba), 1-(4-chloro-o-sulfo-5-tolylazo)-2-naphtholarium)
* Red No. 205 (Lithol Red, Pigment Red 49(Na), monosodium 2-(2-hydroxy-1-naphthylazo)-1-naphthalenesulfonate)
* Red No. 206 (Lithol Red CA, Pigment Red 49, calcium 2-(2-hydroxy-1-naphthylazo)-1-naphthalenesulfonate)
* Red No. 207 (Lithol Red BA, Pigment Red 49(Ba), barium 2-(2-hydroxy-1-naphthylazo)-1-naphthalenesulfonate)
* Red No. 208 (Lithol Red SR, Pigment Red 49(Sr), strontium 2-(2-hydroxy-1-naphthylazo)-1-naphthalenesulfonate)

* Red No. 213 (Rhodamine B, Basic Violet 10, 9-o-carboxyphenyl-6-diethylamino-3-ethylimino-3-isoxanthene-3-ethochloride)
* Red No. 214 (Rhodamine B acetate, Basic Violet 10, 9-o-carboxyphenyl-6-diethylamino-3-ethylimino-3-isoxanthene-3-ethoacetate)
* Red No. 215 (Rhodamine B stearate, Solvent Red 49, 9-o-carboxyphenyl-6-diethylamino-3-ethylimino-3-isoxanthene-3-ethostearate)
* Red No. 218 (Tetrachlorotetrabromofluoresceine, Solvent Red 92, 2,4,5,7-tetrabromo-12,13,14,15-tetrachloro-3,6-fluorandiol)
  Red No. 219 (Brilliant Lake Red R, Pigment Red 64, calcium 3-hydroxy-4-phenylazo-2-naphthoate)
* Red No. 220 (Deep maroon, Pigment Red 63(Ca), calcium 4-(1-sulfo-2-naphthylazo)-3-hydroxy-2 naphthoate)
* Red No. 221 (Toluidine Red, Pigment Red 3, 1-(o-nitro-p-tolylazo)-2-naphthol)
* Red No. 223 (Tetrabromofluoresceine, Solvent Red 43, 2,4,5,7-tetrabromo-3,6.fluorandiol)
* Red No. 225 (Sudan 111, Solvent Red 23, 1-p-phenylazophenylazo-2-naphthol)
* Red No. 226 (Helindon Pink CN, Vat Red 1, 5,5,'-dichloro- 3,3'-dimethylthioindigo)
* Red No. 227 (Fast Acid Magenta, Acid Red 33, disodium 8-amino-2-phenylazo-1-naphthol-3,6-disulfonate)
* Red No. 228 (Permatone Red, Pigment Red 4, 1-(o-chloro-p-nitrophenylazo)-2-naphthol)
* Red No. 230-(1) (Eosine YS, Acid Red 87, 9-o-carboxyphenyl-6-hydroxy-2,4,5,7-tetrabromo-3-isoxanthonedisodium)
* Red No. 230-(2) (Eosine YSK, Acid Red 87, 9-o-carboxy phenyl-6-hydroxy-2,4,5,7-tetrabromo-3-isoxanthonedipotassium)
* Red No. 231 (Phloxine BK, Acid Red 92, 9-(3,4,5,6-tetrachloro-o-carboxyphenyl)-6-hydroxy-2,4,5,7-tetrabromo-3-isoxanthonedipotassium)
* Red No. 232 (Rose Bengale K, Acid Red 94, 9-(3,4,5,6-tetrachloro-o-carboxyphenyl)-6-hydroxy-2,4,5,7-tetraiodo-3-isoxanthonedipotassium)
* Orange No. 201 (Dibromofluoresceine, Solvent Red 72, 4,5-dibromo-3,6-fluorandiol)
* Orange No. 203 (Permanent Orange, Pigment Orange 5, 1-(2,4-dinitrophenylazo)-2-naphthol)
* Orange No. 204 (Benzidine Orange G, Pigment Orange 13, 3,3'-dichlorodiphenyl-4,4'-bisazo-(1-phenyl-3-methyl-5-pyrazolone))
* Orange No. 205 (Orange II, Acid Orange 7, 1-p-sulfophenylazo- 2-naphtholmonosodium)
* Red No. 401 (Violamine R, Acid Violet 9, 9-o-carboxyphenyl-6-(4-sulfo-o-tolylimino-3-isoxanthenedisodium)
* Red No. 404 (Brilliant Fast Scarlet, Pigment Red 24, 1-(4-nitro-2-tolylazo)-2-hydroxy-3-naphthoic acid anilide)
* Yellow No. 405 (Permanent Red F5R, Pigment Red 48, calcium 1-(3-chloro-6-sulfo-4-tolylazo)-2-hydroxy-3-naphthoate)
* Red No. 501 (Drug Scarlet, Solvent Red 24, o-tolylazo-o-tolylazo-2-naphthol)
* Red No. 502 (Ponceau 3R, Food Red 6, disodium 1-pseudocumylazo-2-naphthol-3,6-disulfonate)
* Red No. 503 (Ponceau R, Acid Red 26, disodium 1-xylylazo-2-naphthol-3,6-disulfonate)
* Red No. 504 (Ponceau SX, Food Red 1, disodium 2-(5-sulfo-2,4-xylylazo)-1-naphthol-4-sulfonate)
* Red No. 505 (Oil Red XO, Solvent Orange 7, 1-xylylazo-2-naphthol)
* Red No. 506 (Fast Red S, Acid Red 88, monosodium 4-(2-hydroxy-1-naphthylazo)-1-naphthalenesulfonate)
* Orange No. 401 (Hansa Orange, Pigment Orange 1, α-(o-nitro-p-anisylazo)-o-acetoacetotoluide)
* Orange No. 402 (Orange I, Acid Orange 20, 4-p-sulfophenylazo-1-naphtholmonosodium)
* Fluoresceine
* Orange No. 403 (Orange SS, Solvent Orange 2, 1-o-tolylazo-2-naphthol)
* Yellow No. 401 (Hansa Yellow, Pigment Yellow 1, α-(o-nitro-p-tolylazo)acetoacetanilide)

These pigments can be used singly, or at least two of them are usable in admixture. The amount of pigment is so determined that the preparation obtained will have a hue in the above-specified range. The pigment is used usually in an amount of about 0.05 to about 4 wt. %, preferably about 0.08 to about 2 wt. %, based on the present composition.

It is essential that the fly attracting composition of the present invention be in a granular form having a mean grain size of about 0.5 to about 5 mm. The composition fails to achieve the contemplated high attracting effect if less than 0.5 mm in mean grain size, e.g. powdery or more than 5 mm. The fact that the grain size of the preparation affects the fly attracting effect has never been reported: it is our research that revealed this for the first time. Preferably, the present composition is in the range of about 1 to about 3 mm in grain size. The composition is not limited specifically in configuration, weight, etc. provided that it has the above-specified grain size. For example, the composition can be in the form of granules, pellets or spherical or disklike grains, amorphous or of any desired shape.

Insecticides can be incorporated into the fly attracting composition of the present invention so as to effectively and efficiently kill the attracted flies. While various insecticides are usable for this purpose which have an insecticidal effect on flies, pyrethroid, organic phosphorus and carbamate insecticides are desirable. Examples of such insecticides are as follows.

* 3-Allyl-2-methylcyclopenta-2-ene-4-one-1-yl cis-/transchrysanthemate (common name: allethrin)
* 3-Allyl-2-methylcyclopenta-2-ene-4-one-1-yl transchrysanthemate (common name: Bioallethrin)
* 5-Benzyl-3-furylmethyl d-cis/trans-chrysanthemate (common name: Resmethrin)
* 5-(2-Propargyl)-3-furylmethyl chrysanthemate (common name: Furamethrin)
* 3-Phenoxybenzyl cis/trans-3-(2,2-dichlorovinyl)-2,2-dimethylcyclopropane carboxylate (common name: Permethrin)
* 3-Phenoxybenzyl cis/trans-chrysanthemate (common name: Phenothrin)
* O,O-Dimethyl O-(2,2-dichloro)vinylphosphate (DDVP)
* O-Isopropoxyphenyl methylcarbamate (common name: Propoxur)
* O,O-Dimethyl O-(3-methyl-4-nitrophenyl)phosphorothioate (common name: Fenitrothion)
* O,O-Diethyl O-2-isopropyl-4-methyl-pyrimidyl(6)-thiophosphate (common name: Diazinon)
* N-(3,4,5,6-Tetrahydrophthalimido)-methyl dl-cis/transchrysanthemate (common name: Phthalthrin)
* O,O-Dimethyl S-(1,2-dicarboethoxyethyl)-dithiophosphate (common name: Malathion)

* α-Cyano-3'-phenoxybenzyl c-isopropyl-4 chlorophenylacetate (common name: Fenvalerate)
* O-(4-Bromo-2,5-dichlorophenyl) O,O-dimethylphosphorothioate (common name: Bromophos)
* S-Methyl N-(methylcarbamoyloxy)thioacetimidate (common name: Methomyl)
* O,O-Dimethyl O-4-methylthio-m-toluylphosphorothioate (brand name: Baycid) (common name: Fenthion)
* Dimethyl-(2,2,2-trichloro-1-hydroxyethyl)phosphonate (common name: Trichlorfon)
* O-2,4-Dichlorophenyl O-ethyl-S-propyl-phosphorodithioate (common name: Prothiophos)

Among these insecticidal compounds, pyrethroid compounds are especially preferable. Of the compounds of this type, the most preferable are 5-benzyl-3-furylmethyl d-cis/trans-chrysanthemate, phenothrin and permethrin. These insecticides are used singly, or at least two of them are used in admixture. The proportion of the insecticide to be used is usually in the range of about 0.1 to about 15 wt. % based on the entire weight of the present composition although not limited specifically.

The fly attracting composition of the present invention is prepared by admixing a suitable carrier with the components and shaping or granulating the mixture into a suitable form having a mean grain size in the foregoing range. Examples of useful carriers are finely divided inorganic substances such as talc, kaolin, silicic acid, active carbon, bentonite, silica, alumina, alumina-silica, calcium carbonate, earthen or porcelaneous powder and kieselguhr, and organic substances such as pulp, fiber, wood powder, sugar powder, soybean flour, wheat flour, starch, resin and rubber.

Preferably, the fly attracting composition of the present invention is prepared, for example, by mixing together the pigment and the attracting compound serving as an active component, along with a suitable insecticide when required, using a solvent and/or a binder solution, granulating the mixture to a specified grain size, removing the solvent and drying the granular product. Examples of solvents useful for this method are alcohols such as methanol and ethanol, ketones such as acetone and methyl ethyl ketone, ethers such as tetrahydrofuran and dioxane, and other substances such as hexane, kerosene, paraffin, petroleum benzine, toluene, ethyl acetate and dichloroethane. Examples of useful binders are cellulose derivatives such as nitrocellulose, hydroxypropylcellulose, acetylcellulose, acetylbutyrylcellulose and methylcellulose, polyvinyl alcohol, gum arabic, sodium carboxymethylcellulose, casein, gelatin, alginic acid. Such binder is adantageously usable usually in the form of about 1 to about 20% aqueous solution.

Also usable as incorporated in the fly attracting composition of the present invention when so required are various known additives such as synergist, antioxidant, decomposition preventing agent, bactericide, fungicide, accidental ingestion preventing agent, etc. Other known attractants are also usable conjointly.

Examples of useful synergists are N-(2-ethylhexyl)-bicyclo[2,2,1]-5-heptene-2,3-dicarboximide, 6-(propylpiperonyl)butyl carbityl ether, etc. Examples of useful antioxidants are butylhydroxyanisole, dibutylhydroxytoluene, tocopherol, γ-oryzanol, etc. Examples of useful decomposition preventing agents are phenylglycldyl ether, etc. These agents, all known, are used in the usual manner and can be used in combination.

Examples of useful bacteriocides are salicylic acid, benzoic acid, sorbic acid, p-chloro-m-xylenol, 2-(4'-thiazoyl)benzimidazole, etc. Examples of useful fungicides are α-bromo cinnamic aldedhyde, N-dimethyl-N-phenyl-N'-(fluorodichloromethyl)thiosulfamide, etc. Examples of useful accidental ingestion preventing agents are tincture of *Capsicum annum,* Japanese bitter wood, chloramphenicol, etc. The proportions of these agents to be used can be determined suitable. For example, accidental ingestion preventing agent can be used in an amount of about 0.1 to about 3 wt. % based on the preparation to be obtained.

Examples of attractants which can be incorporated into the present fly attracting composition are ingestion-inducing substances including protein- and/or carbohydrate-containing substances such as milk powder, egg powder, pupal powder, krill powder, meat extract, albumin, globulin, amino acids (e.g. proline), malt extract, caramel, vanillin, whey, cereal flours, yeast, glucose, sucrose, maltose, monosaccharides and disaccharides. Examples of other useful attractants are terpineol, farnesol, geraniol, acetic acid, isovaleric acid, trimethylamine, indole, piperidine, phenylethanol, ammonium carbonate, skatole, formaldehyde, hexamethylenetetramine, ammonium carbamate, papain, butyric acid, isovaleraldehyde, ethylamine, aliphatic monoesters of chlorinated alkene polyols, pancreatin. The amounts of these attractants to be used can be determined suitably and are not limited specifically.

The preferred embodiments of the present invention include a bait composition having incorporating therein at least one pyrethroid insecticide selected from the group consisting of (5-benzyl-3-furyl)methyl d-cis/trans-chrysanthemate (common name: allethrin), 3-phenoxybenzyl cis/trans-chrysanthemate (common name: phenothrin) and 3-phenoxybenzyl cis/trans-3-(2,2-dichlorovinyl)-2,2-dimethyl-cyclopropane carboxylate (common name: permethrin).

Generally, bait compositions comprise a food for flies impregnated with or incorporating an insecticide. To achieve a satisfactory result, the bait composition must meet the following requirements. First, the insecticidal component selected should be least repellent to flies. Second, there must be physical and/or chemical means for attracting flies to the bait. Third, the bait needs to be fully attractive to the taste so as to induce the attracted fly to ingest the bait. Fourth, the bait must be taken in by the fly at a sufficient lethal dose before disgusting the fly in some way or producing toxic symptoms. These requirements are not independent of, but are closely associated with, one another, when failing to fulfill any one of these requirements, the bait composition exhibits a seriously reduced effect and produces no satisfactory result.

The insecticidal components of bait compositions presently known are limited only to some of organic phosphorus or carbamate insecticides, and pyrethroid insecticides are not used commonly. Pyrethroid insecticides generally are known to quickly act on adults of flies (hereinafter referred to merely as "flies") to produce an outstanding knockdown effect because the insecticide enters the body of the fly through the skin or stoma and quickly acts on the nervous system. Accordingly, the application of insecticides of this type is limited only to the stomatal respiratory tract and the cutaneous contact tract. Utilizing the above characteristics, pyrethroid insecticides are used not only for flies but also for mosquitos, cockroaches, etc., in the form of preparations such as mosquito-repellent insence (stomatal tract), mosquito-repellent electric mat (same), aerosol (stomatal tract and cutaneous contact tract), fumigant or vaporizable composition (same), etc. However, they have not been used in the form of insecticidal bait compositions for the oral tract.

An attempt to use pyrethroid insecticides for the oral tract to control insects is reported, for example, by J. Keiding in Danish Pest Infection Laboratory Annual Report, 1978, "Paint-on-Baits" Laboratory Tests, but the report says the baits incorporating pyrethroid insecticides failed to achieve a satisfactory result. The reported result appears reasonable in view of the prevailing scientific information that the pyrethroid insecticides are not ingestible by insects. Further recently, it has been reported that 2,2-dimethyl-3-($\beta$,$\beta$-dichlorovinyl)-cyclopropanecarboxylic acid $\alpha$-cyano-3-phenoxy-4-fluorobenzene, a kind of pyrethroid insecticide, is effective for baits for flies (see Unexamined Japanese Patent Publication SHO 59-78111). However, the report says that the above-mentioned compound alone is effective and that the other pyrethroid insecticides are not suited to baits. Thus, it is presently generally believed in the art that the pyrethroid insecticides have insect-repellent activity but are less effective when taken in orally.

Nevertheless, our research has demonstrated that when the fly attracting composition of the present invention has incorporated therein at least one of the foregoing three pyrethroid compounds and is used as a bait composition, the pyrethroid compound exhibits a powerful insecticidal effect on flies although taken in orally and further that the composition efficiently attracts flies without arousing any aversion and induces the attracted flies to positively take in a lethal dosage of the bait with great tenacity, consequently achieving a high controlling efficiency.

Attractants for inducing flies to ingest the present bait composition are incorporated into the composition. The attractants already exemplified are usable as such attractants. The ingestion-inducing attractant is a substance which itself is eatable by flies. Useful carriers are preferably edible substances such as sugar powder, soybean flour, wheat flour, starch, etc. The ingestion-inducing attractant and/or the edible substance serving as a carrier are used in an amount of at least 70 wt. % based on the composition.

The above-mentioned pyrethroid insecticidal compounds are usable singly, or at least two of them can be used in combination, the amount thereof being 0.1 to 15 wt. %, preferably 0.3 to 10 wt. %, based on the composition. It is especially preferable to use allethrin.

The sex pheromone is used in an amount of about 0.01 about 15 wt. %, preferably about 0.02 to about 4 wt. %, based on the composition. Although the pyrethroid insecticidal compound and the sex pheromone are usable in a ratio which is not limited particularly but is selectable from a wide range, the former to latter ratio (by weight) is usually about 1:0.001-1, preferably about 1:0.005-0.5.

The same additives as already mentioned are usable for preparing the bait composition. The components can be made into a granular preparation in the same manner as already described.

The attractant composition of the present invention is usable in the original granular form, or as adhered to a suitable substrate, such as paper, fabric, and film, sheet, plate, ball, polygonal body or the like of synthetic resin, wood or metal.

Like common fly controlling or destroying agents, the fly attracting composition of the present invention, when prepared with the insecticide, etc. incorporated therein, is usable by placement, spreading or adhering in fly occurring areas such as agricultural crop growing fields, orchards, greenhouses, vinyl houses, cattle sheds, poultry houses, grain storehouses, kitchens, dwelling houses, etc. When not containing the insecticide or the like, the present composition is usable in these places in combination with other known suitable insecticidal preparation or the like. The amount of the composition to be used can be determined suitably in accordance with the method and place of application. For example, when to be applied by spreading, the present fly attracting composition is used in such an amount that at least 1 mg, preferably about 3 to about 10 mg, of the active compound will be present per square meter of the area concerned.

Examples of flies attractable by the present attractant composition are those of the family Muscidae such as *Musca domestica, Muscina stabulans, Stomoxys calcitrans* and *Ophyra leucostoma:* Fanniinae: the family *Calliphoridae* such as *Calliphora lata, Aldrichina grahami, Phaenicia sericata, Phaenicia cuprina, Lucilia caesar, Lucilia illustris, Chrysomyia megacephala* and *Phormia regina:* the family Sarcophagidae such as *Sarcophaga peregrina* and *Parasarcophaga similis:* the family *Drosophilidae* such as *Drosophila melanogaster* and *Drosophila virilis:* the family Piophilidae such as *Piophila casei:* the family Scatophagidae such as *Scatophaga stercoraria:* the family Dromyzidae such as *Stenodryomyza formosa:* the family Phoridae such as *Megaselic scalaris:* etc.

EXAMPLE

The present invention will be described in greater detail with reference to the following examples.

| | | |
|---|---|---|
| 1. Sugar powder | 60 | g |
| 2. Pigment | 0.8 | g |
| 3. cis-9-Tricosene | 15 | mg |
| (1.5 ml as 1 wt. % acetone solution) | | |
| 4. Mixture of methanol and acetone in equal amounts | 100 | ml |
| 5. Binder | 7 | ml |
| (20 wt. % aqueous solution of gum arabic) | | |

The above components 1 to 5 were mixed together with stirring, the solvent was evaporated off by a rotary evaporator (50° C.) and the mixture was screened with a 2-mm-mesh sieve. The oversize portion was also crushed to particle. With addition of an aqueous solution of binder by spraying, the resulting mixture was thoroughly kneaded and made into grains, about 2 mm in mean size, under pressure. The granular mixture was allowed to stand at room temperature for at least 12 hours and dried to obtain a granular preparation. In this way, fly attracting compositions 1a to 1m were obtained.

The cis-9-tricosene concentration of these preparation specimens was 0.025 wt. %.

The preparation specimens obtained were checked for hue according to JIS Z 8721. Table 1 shows the results.

TABLE 1

| Preparation No. | Pigment | Hue of preparation |
| --- | --- | --- |
| 1a | Tartrazine No. 4 | 6 YR |
| 1b | Uranine K (202-1) | 2 Y |
| 1c | Naphthol Yellow S | 3 Y |
| 1d | Fluoresceine | 1 YR |
| 1e | Quinoline Yellow SS | 10 YR |
| 1f | Fast Yellow 3G | 7 YR |
| 1g | Uranine K (202-2) | 2 Y |
| 1h | Benzidine Yellow G | 5 YR |
| 1i | Metanil Yellow | 5 Y |
| 1j | Hansa Yellow | 3 Y |
| 1k | Yellow No. 5 | 9 R |
| 1l | Sunset Yellow F | 1 YR |
| 1m | Yellow No. 4 | 1.5 R |

EXAMPLE 2

Fly attracting granular compositions 2a to 2m having an insecticide concentration of 1 wt. % were prepared in the same manner as in Example 1 with the exception of additionally using as another insecticidal component 600 mg of Methomyl (S-methyl N-(methylcarbamoyloxy)thioacetimiate carbamate insecticide, product of E.I. du Pont de Nemours & Co.).

Each of the preparation specimens obtained was found to have the same hue as the corresponding one of the specimens 1a to 1m (see Table 1) of Example 1.

The preparations obtained in Example 2 were tested for attracting effect by the following methods.

Test I

The preparations were placed, each in an amount of 60 g, into glass dishes (15.5 cm in diameter) individually, which were then arranged on the floor of a test room along a circle, as spaced apart from one another at a distance of about 30 cm. Houseflies (*Musca domestica*) were released into the test room. Upon the lapse of a predetermined period of time, the number of dead flies within each dish was checked.

The fly attracting effect of each preparation was evaluated in terms of the ratio (%) of the number of dead flies in the dish containing the preparation to the total number of dead flies in the test room (i.e. the total of the numbers of dead flies in all dishes).

Test II

The fly attracting effect of the preparations was evaluated in the same manner as in Test I with the exception of placing the preparations, 10 g each, into plastics cups individually and arranging the cups on the floor of a glass chamber (1.45 m×1.4 m) placed outdoors, as spaced apart from one another at a distance of about 20 cm.

The test results are given in Table 2 (Test I) and Table 3 (Test II).

TABLE 2

| Preparation No. | Fly attracting effect (%) |
| --- | --- |
| 2a | 1 |
| 2b | 3 |
| 2c | 2 |
| 2d | 28 |
| 2e | 3 |
| 2f | 4 |
| 2g | 4 |
| 2h | 4 |
| 2i | 3 |
| 2j | 3 |
| 2k | 30 |
| 2l | 11 |
| 2m | 3 |
| Control | 1 |
| 2a | 3 |
| 2b | 2 |
| 2c | 1 |
| 2d | 16 |
| 2e | 4 |
| 2f | 5 |
| 2g | 5 |
| 2h | 3 |
| 2i | 3 |
| 2j | 5 |
| 2k | 28 |
| 2l | 21 |
| 2m | 3 |
| Control | 1 |

EXAMPLE 3

Fly attracting-insecticidal compositions were prepared in the same manner as in Example 2 except that 0.08 wt. % or 1.3 wt. % of Sunset Yellow F was used. The preparations obtained were tested for fly attracting effect in the same manner as in Example 2, Test I. Table 4 shows the result.

TABLE 4

| Preparation No. | Pigment Name | Concn. (wt. %) | Hue | Fly attracting effect (%) |
| --- | --- | --- | --- | --- |
| 3a | Sunset Yellow F | 0.08 | 1 YR | 12 |
| 3b | " | 1.3 | 1 YR | 16 |

EXAMPLE 4

| | |
| --- | --- |
| Pigment (Fluoresceine) | 1 g |
| Insecticide (Permethrin) | 1 g |
| cis-9-Tricosene | 25 mg |
| Extender (sugar powder) | 100 g |

The specified amounts of the pigment, cis-9-tricosene (used as 1 ml of hexane solution) and sugar powder were mixed together with stirring, and the solid mixture obtained was crushed, thoroughly kneaded with addition of 20% aqueous solution of gum arabic by spraying, granulated under pressure and dried at room temperature.

The insecticide as dissolved in acetone was then sprayed to the mixture obtained in an amount of 15 ml per g of the mixture. The mixture was thoroughly stirred, and the solvent was removed therefrom by a rotary evaporator (50° C.) to obtain a fly attracting composition of the invention. This composition will be referred to as "invention 4a".

COMPARATIVE EXAMPLE 1

A comparative fly attracting composition, having the same hue and the same mean grain size as the composition of Example 4, was prepared in the same manner as in Example 4 except that cis-9-tricosene was not used. This composition will be referred to as "comparative 4b".

COMPARATIVE EXAMPLE 2

The components used in Example 4 were mixed together with stirring, then pulverized and dried to obtain a comparative fly attracting composition in the form of a powder. This composition will be referred to as "comparative 4c".

Attracting-insecticidal test

The attractant specimens prepared above were tested for attracting-insecticidal activity on flies by placing the specimens, 20 g each, into large dishes, 15 cm in inside diameter, individually, arranging the dishes on the floor of a test room (4×3×2.6 m) and releasing about 140 to 150 flies into the room. The number of dead flies in each dish was counted one to two hours after the start of the test. The activity is evaluated in terms of the average obtained by repeating the above test four times for each specimen.

Table 5 below shows the result.

TABLE 5

| Test No. | Specimen | Attracting-insecticidal activity (number of flies) |
|---|---|---|
| 1 | Invention 4a | 69.1 |
| 2 | Comparative 4b | 9.1 |
| 3 | Comparative 4c | 2.9 |

With reference to Table 5, comparison between invention 4a and comparative 4c, having the same composition, reveals that invention 4a is exceedingly superior in the activity owing to the feature of the preparation that it is given the specified grain size by granulation. In this effect, the preparation of the invention is also exceedingly superior to comparative 4b which is free from cis-9-tricosene. Thus, the test result indicates that the outstanding attracting effect is attributable to the use of cis-9-tricosene and also to the specified grain size.

EXAMPLE 5

| | |
|---|---|
| Insecticide (Methomyl, S—methyl N—(methylcarbamoyloxy)thioacetimidate | 2 g |
| cis-9-Tricosene | 50 mg |
| Sugar powder | 100 g |
| Antioxidant (BHT, 2,6-di-tert-butylmethylphenyl) | 2 g |
| Fluoresceine | 1 g |

The sugar powder and cis-9-tricosene (used as 1 ml of hexane solution) were mixed together with stirring to obtain a solid mixture, which was then crushed, thoroughly kneaded with addition of 20% aqueous solution of gum arabic by spraying, granulated to a mean grain size of 2 mm under pressure and dried at room temperature.

The above insecticide as dissolved in acetone was subsequently sprayed to the granular mixture in an amount of 15 ml per 50 g of the mixture. The mixture was thoroughly stirred, and the solvent was removed therefrom by a rotary evaporator (50° C.) to obtain a fly attracting composition of the invention. This composition will be referred to as "invention 5a".

The composition has a hue of 1YR and was eventually 1.5 mm in mean grain size.

COMPARATIVE EXAMPLE 3

A comparative fly attracting composition having the same hue and mean grain size as above was prepared in the same manner as in Example 5 except that no cis-9-tricosene was used. The composition will be referred to as "comparative 5b".

Attracting-insecticidal test

The composition specimens obtained in these examples were tested in the same manner as in Example 4 using 20 g of each specimen. Table 6 below shows the result. The activity is evaluated in terms of the average obtained by repeating the test procedure five times for each specimen.

TABLE 6

| Test No. | Specimen | Attracting-insecticidal activity (number of flies) |
|---|---|---|
| 1 | Invention 5a | 43.3 |
| 2 | Comparative 6b | 10.4 |

EXAMPLES 6–11

In the same manner as in Example 4, attracting compositions of the invention having different grain sizes were prepared using the components listed in Table 7.

The symbols used in Table 7 for some of the components represent the following.

Pigments
A-1: Sunset Yellow
A-2: Yellow No. 2
A-3: Fluoresceine

Insecticides
B-1: Permethrin
B-2: Chrysron-Forte (compound name: 5-benzyl-3-furylmethyl d-cis/trans-chrysanthemate)
B-3: Phenothrin

TABLE 7

| Ex. No. | cis-9-Tricosene Amount (part) | Insecticide Name | Insecticide Amount (parts) | Pigment Name | Pigment Amount (parts) | Sugar powder Amount (parts) | Grain size (mm) | Hue |
|---|---|---|---|---|---|---|---|---|
| 6 | 0.025 | B-1 | 1.0 | A-1 | 1.0 | 97.975 | 1.5 | 1 YR |
| 7 | 0.025 | B-2 | 1.0 | A-2 | 1.0 | 97.975 | 1.5 | 9 R |
| 8 | 0.025 | B-3 | 1.0 | A-3 | 1.0 | 97.975 | 1.5 | 1 YR |
| 9 | 0.025 | B-1 | 3.0 | A-1 | 3.0 | 93.975 | 3.0 | 1 YR |
| 10 | 0.025 | B-2 | 3.0 | A-1 | 3.0 | 93.975 | 3.0 | 1 YR |
| 11 | 0.025 | B-3 | 3.0 | A-1 | 3.0 | 93.975 | 3.0 | 1 YR |

The composition specimens of the invention prepared in these examples were tested for attracting-insecticidal activity on flies in the same manner as in Example 4. The result achieved by each of the specimens was comparable to those already attained by the compositions of the invention.

EXAMPLES 12–17

Granular attracting-insecticidal compositions having a mean grain size of 2 mm and the same hue as the composition of Example 4 according to the invention were prepared in the same manner as in Example 4 with the exception of using the sex pheromones listed in Table 8 below in place of cis-9-tricosene.

TABLE 8

| Example No. | Sex pheromone |
| --- | --- |
| 12 | 9-Tricosene |
| 13 | 10-Methyl-9-tricosene |
| 14 | cis-2-Methyl-8-docosene |
| 15 | cis-9-Docosene |
| 16 | cis-8-Docosene |
| 17 | cis-10-Tricosene |

The compositions obtained were tested in the same manner as in Example 4. Consequently, each of the composition was found to exhibit the same attracting effect as achieved by the composition of the invention in Example 4.

EXAMPLE 18

A 0.6 g quantity of (5-benzyl-3-furyl)methyl d-cis/-trans-chrysanthemate (hereinafter referred to as "compound A"), 1.04 g of Yellow No. 5, 0.1 g of cis-9-tricosene, 60 g of sugar powder and 20 g of pupal powder were mixed together with stirring. The solvent was removed from the mixture using a rotary evaporator (50° C.). The mixture was screened with a 2-mm-mesh sieve, and the oversize portion was further pulverized to particles. The combined powder thus obtained was fully kneaded with addition of 1.2 ml of Amycol H (aqueous binder solution) by spraying and granulated to a mean grain size of 2 mm under pressure. The granular mixture was dried at 40° C. for 4 hours to obtain a bait composition according to the invention.

EXAMPLE 19

A bait composition of the invention was prepared in the same manner as in Example 18 except that 40 g of pupal powder was used.

EXAMPLE 20

A bait composition of the invention was prepared in the same manner as in Example 18 with the exception of using 10 g of wheat flour and 30 g of glucose in place of sugar powder and 5 g of a meat extract in place of pupal powder.

EXAMPLE 21

A bait composition of the invention was prepared in the same manner as in Example 18 with the exception of using Permethrin in place of compound A.

EXAMPLE 22

A bait composition of the invention was prepared in the same manner as in Example 18 except that Phenothrin was used in place of compound A.

TEST EXAMPLE

Two g of each of the bait compositions obtained in Examples 18, 21 and 22 was placed into a plastics cup (KP-430) containing 100 male adults of flies. The knockdown was checked with the lapse of time. Table 9 shows the result.

TABLE 9

| Example | Knockdown 5 Minutes later | 24 Hours later |
| --- | --- | --- |
| 18 | 100 | 100 |
| 21 | 100 | 100 |
| 22 | 100 | 100 |

We claim:

1. A fly attracting composition comprising:
   (a) as a fly attracting compound, about 0.01 to about 15% by weight, based on the weight of the composition, of at least one sex pheromone selected from the group consisting of 9-tricosene, cis-9-tricosene, 10-methyl-9-tricosene, cis-2-methyl-8-docosene, cis-9-docosene, cis-8-docosene and cis-10-tricosene;
   (b) a colorant to impart a yellowish red color in the range of 2.5R to 2.5YR in hue to the composition; and
   (c) a carrier; the composition being in granular form having a mean grain size of about 0.5 to about 5 mm.

2. A composition as defined in claim 1 wherein the sex pheromone is cis-9-tricosene.

3. A composition as defined in claim 1 wherein the hue is in the range of 7.5R to 2.5YR.

4. A composition as defined in claim 1 wherein the mean grain size is in the range of about 1 to about 3 mm.

5. A composition as defined in claim 1 which further comprises about 0.1 to about 15% by weight based on the weight of the composition of an insecticidal compound.

6. A composition as defined in claim 5 wherein the insecticidal compound is a pyrethroid compound.

7. A composition as defined in claim 6 wherein the insecticidal compound is at least one compound selected from the group consisting of 5-benzyl-3-furylmethyl d-cis/trans-chrysanthemate, 3-phenoxybenzyl cis/trans-chrysanthemate and 3-phenoxybenzyl cis/-trans-3-(2,2-dichlorovinyl)-2,2-dimethylcyclopropanecarboxylate.

8. A composition as defined in claim 7 wherein the insecticidal compound is 5-benzyl-3-furylmethyl d-cis/-trans-chrysanthemate.

9. A composition as defined in claim 7 or 8 which further comprises about 70% by weight or more, based on the weight of the composition of an ingestion-inducing attractant and/or an edible substance as a carrier.

* * * * *